United States Patent [19]

Kosley, Jr. et al.

[11] 4,452,802
[45] Jun. 5, 1984

[54] ANTIHYPERTENSIVE SPIRO[BENZOFURAN-AZALKANES]

[75] Inventors: Raymond W. Kosley, Jr., Bridgewater; Robert J. Cherill, Somerset, both of N.J.

[73] Assignee: Hoechst-Roussel Pharmaceuticals Incorporated, Somerville, N.J.

[21] Appl. No.: 526,193

[22] Filed: Aug. 25, 1983

[51] Int. Cl.³ ............... A61K 31/445; A61K 31/40; C07D 491/10
[52] U.S. Cl. .................. 424/267; 424/274; 546/17; 548/411
[58] Field of Search ............ 546/17; 548/411; 424/267, 274

[56] References Cited

U.S. PATENT DOCUMENTS 4,166,119 8/1979 Effland et al. ............... 546/17
4,166,120 8/1979 Effland et al. ............... 546/17

OTHER PUBLICATIONS

Effland et al., "J. Heterocyclic Chem.", vol. 18 (1981), pp. 811-814.

Primary Examiner—Robert T. Bond
Attorney, Agent, or Firm—Tatsuya Ikeda

[57] ABSTRACT

There are described antihypertensive spiro[benzofuran-azalkanes] of the formula where X is hydrogen or halogen (F, Cl, Br, or I); m and n are each 0, 1 or 2 but m plus n is 1 or 2; and R is k being 2 or 3 and Y being hydrogen or halogen, which are useful as antihypertensive agents and methods for synthesizing the same.

26 Claims, No Drawings

ANTIHYPERTENSIVE SPIRO[BENZOFURAN-AZALKANES]

This invention relates to novel antihypertensive spiro[benzofuran-azalkanes] of the formula

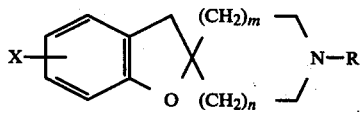

where X is hydrogen or halogen (F, Cl, Br, or I); m and n are each 0, 1 or 2 but m plus n is 1 or 2; and R is

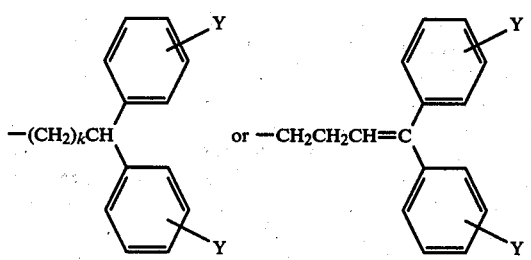

k being 2 or 3 and Y being hydrogen or halogen, which are useful as antihypertensive agents; antihypertensive compositions comprising said compounds or a pharmaceutically acceptable acid addition salt thereof; and methods for synthesizing said compounds.

To the best of our knowledge the compounds of the present invention have not been described or suggested.

Throughout the specification and the appended claims, a given chemical formula or name shall encompass all stereo isomers thereof where such isomers exist.

The compounds of the present invention are prepared by following one or more of the steps described below in which the definitions of X, m, n, R, k and Y are as defined above unless noted to the contrary.

STEP A

Compounds of the general formula

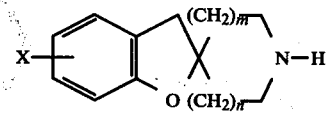

can be prepared by use of the methods described in Effland et al, U.S. Pat. No. 4,166,119 or simple modifications thereof. See also Effland et al, U.S. Pat. No. 4,166,120 and Effland et al, J. Heterocyclic Chem., 18, 811 (1981).

Alternatively, a compound of Formula III can be prepared at a high positional selectivity by reacting a compound of Formula IV with N-bromosuccinimide (NBS), and similarly a compound of Formula V can be prepared at a high positional selectivity by reacting Compound IV with iodine monochloride.

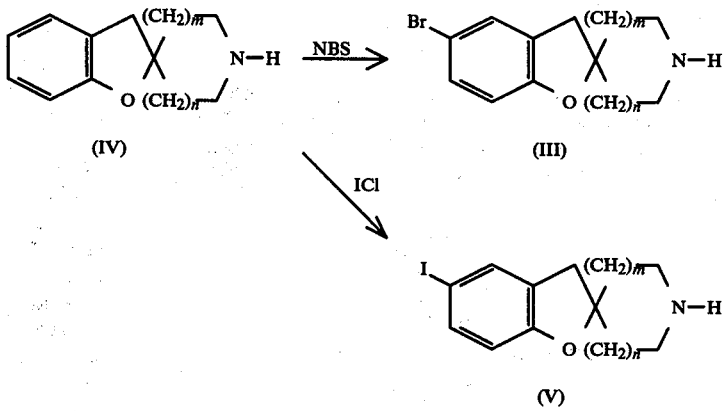

The bromination using N-bromosuccinimide is conducted usually in a suitable solvent such as methanol, a typical reaction condition being stirring the reaction mixture at 5°–25° C. for less than 1 hour.

The iodination using iodine monochloride is conducted usually in a suitable medium such as $H_2O/CH_2Cl_2$, a typical reaction condition being stirring the reaction mixture at room temperature for several hours.

STEP B

A compound of Formula II obtained from STEP A is reacted with a compound of Formula VI where Hal is chlorine or bromine to afford Compound VII of this invention.

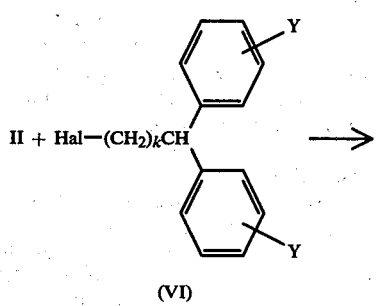

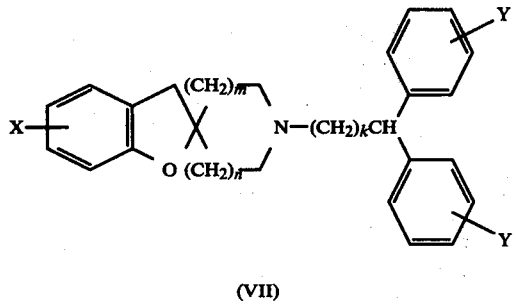

(VII)

Said alkylation reaction is conducted usually in the presence of an optional acid scavenger such as $K_2CO_3$ and optional reaction initiator such as KI in a suitable solvent such as DMF. The reaction temperature may be from room temperature to about 100° C. Typically, the reaction is conducted first at a lower temperature such as 40°-70° C. for about 1 hour or less and then at a higher temperature such as 80°-90° C. for a few hours or less.

STEP C

A Compound of Formula II is reacted with a compound of Formula VIII to afford Compound IX of this invention. Said alkylation reaction is conducted in substantially the same manner as described in STEP B.

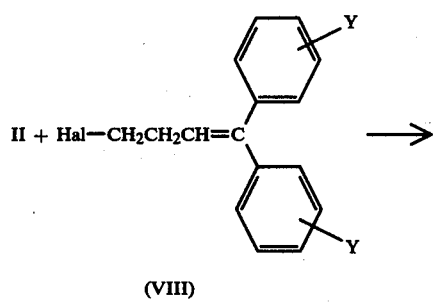

(VIII)

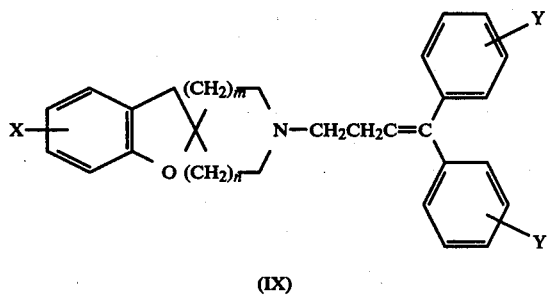

(IX)

All other starting materials shown above are either known compounds or easily prepared by routine methods known to the art from readily available materials.

The spiro[benzofuran-azalkanes] of the present invention are useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure is measured on the third day following administration. The antihypertensive activities of some of the compounds, expressed as a decrease in mean arterial blood pressure (in mm Hg), are given in Table I.

TABLE 1
ANTIHYPERTENSIVE ACTIVITY

| Compound | Dose mg/kg p.o. | Blood Pressure Drop mm Hg |
| --- | --- | --- |
| 1'-[4,4-Bis(4-fluorophenyl)butyl]-5-bromospiro[benzofuran-2(3H)4'-piperidine]oxalate | 3 | 50 |
| 1'-[4,4-Bis(4-fluorophenyl)butyl]-spiro[benzofuran-2(3H)4'-piperidine]-hydrochloride | 3 | 40 |
| 1'-[4,4-Bis(4-fluorophenyl)3-butenyl]-5-chlorospiro[benzofuran-2(3H)4'-piperidine]oxalate | 10 | 35 |
| 1'-[4,4-Bis(4-fluorophenyl)butyl]-5-chlorospiro[benzofuran-2(3H)4'-piperidine]oxalate | 3 | 39 |
| 1'-(4,4-Diphenylbutyl)-5-chlorospiro-[benzofuran-2(3H)4'-piperidine]oxalate | 50 | 18 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
1'-[4,4-Bis(4-fluorophenyl)butyl]-5-bromospiro[benzofuran-2(3H)4'-piperidine]oxalate;
1'-[4,4-Bis(4-fluorophenyl)butyl]spiro[benzofuran-2(3H)4'-piperidine]hydrochloride;
1'-[4,4-Bis(4-fluorophenyl)-3-butenyl]-5-chlorospiro[benzofuran-2(3H)4'-piperidine]oxalate;
1'-[4,4-Bis(4-fluorophenyl)butyl]-5-chlorospiro[benzofuran-2(3H)4'-piperidine]oxalate;
1'-(4,4-Diphenylbutyl)-5-chlorospiro[benzofuran-2(3H)4'-piperidine]oxalate;
1'-[4,4-Bis(4-fluorophenyl)butyl]-5-iodospiro[benzofuran-2(3H)4'-piperidine]hydrochloride; and
1'-(4,4-Diphenylbutyl)spiro[benzofuran-2(3H)4'-piperidine]hydrochloride.

The following examples are given for illustrative purposes and are not to be considered as limiting the invention disclosed herein. All temperatures are given in degrees Celcius.

EXAMPLE 1

5-Bromospiro[benzofuran-2(3H)4'-piperidine]hydrochloride

To 700 ml of methanol was added 40.00 g (0.177 mol) of spiro[benzofuran-2(3H)4'-piperidine]hydrochloride and the solution was cooled in ice to 5° C. To it with stirring was added at once 30.00 g (0.169 mol) of N-bromosuccinimide. The solution was warmed to ambient temperature during which time the reaction was completed. The solvent was evaporated to a solid. The solid was partitioned between dichloromethane and saturated aqueous sodium bicarbonate solution. The dichloromethane layer was separated, washed with the saturated aqueous salt solution, dried over sodium sulfate and filtered. The hydrochloride salt was formed by adding excess ethereal HCl to the dichloromethane solution. The product precipitated out of the solution. It was filtered, washed with dichloromethane and dried at 110° C. under vacuum to yield 34.4 g (64%) of product, m.p. 231°–232° C.

ANALYSIS: Calculated for $C_{12}H_{15}BrClNO$: 47.32%C, 4.96%H, 4.60%N; Found: 46.88%C, 4.86%H, 4.54%N.

EXAMPLE 2

1'-[4,4-Bis(4-fluorophenyl)butyl]-5-bromospiro[benzofuran-2(3H)4'-piperidine]oxalate A suspension of 5.0 g (16.4 mmol) of 5-bromospiro[benzofuran-2(3H)4'-piperidine]hydrochloride, 6.0 g (19.7 mmol) of potassium carbonate, 0.43 g of potassium iodide, 20 ml of DMF and 5.28 g (18.8 mmol) of 4,4-bis(4-fluorophenyl)butyl chloride was stirred at 50°–60° C. for 45 minutes and at 80°–90° C. for 1 hour. The mixture was poured into ice/water/ether, extracted twice with ether, washed with water and with saturated sodium chloride and dried over potassium carbonate. Filtration followed by evaporation of the solvent provided 9.7 g of an oil. The oil was dissolved in ether and filtered through 200 g of alumina. Evaporation of the solvent from the effluent provided an oil, the oxalate of which was recrystallized from methanol to provide 3.6 g (5.98 mmol, 30.3%) of 1'-[4,4-bis(4-fluorophenyl)butyl]-5-bromospiro[benzofuran-2(3H)4'-piperidine]oxalate, m.p. 198°–200° C.

ANALYSIS: Calculated for $C_{28}H_{28}BrF_2NO.C_2H_2O_4$: 59.80%C, 5.02%H, 2.33%N; Found: 59.64%C, 5.01%H, 2.16%N.

EXAMPLE 3

1'-[4,4-Bis(4-fluorophenyl)butyl]spiro[benzofuran-2(3H)4'-piperidine]hydrochloride A suspension of 5.0 g (22.1 mmol) of spiro[benzofuran-2(3H)4'-piperidine]hydrochloride, 9.15 g (66.3 mmol) of potassium carbonate, 0.66 g of potassium iodide, 30 ml of DMF and 7.27 g (25.9 mmol) of 4,4-bis(4-fluorophenyl)butyl chloride was stirred at room temperature for 2 hours and subsequently at 80°–90° under nitrogen for 2 hours. The mixture was allowed to cool to room temperature, poured into water/ether, extracted twice with ether, washed with water and saturated sodium chloride and dried over potassium carbonate. Filtration followed by evaporation of the solvent provided an oil. The oil was dissolved in ether and filtered through 200 g of alumina. Evaporation of the solvent from the effluent provided an oil, the hydrochloride of which was recrystallized from ethanol to provide 5.07 g (10.8 mmol, 48.8%) of 1'-[4,4-bis(4-fluorophenyl)butyl]spiro[benzofuran-2(3H)4'-piperidine]hydrochloride, m.p. 220°–222° C.

ANALYSIS: Calculated for $C_{28}H_{29}F_2NO.HCl$: 71.55%C, 6.43%H, 2.98%N; Found: 71.22%C, 6.46%H, 2.86%N.

EXAMPLE 4

1'-[4,4-Bis(4-fluorophenyl)-3-butenyl]-5-chlorospiro[benzofuran-2(3H)4'-piperidine]oxalate A suspension of 6.0 g (23.1 mmol) of 5-chlorospiro[benzofuran-2(3H)4'-piperidine]hydrochloride, 11.0 g (79.7 mmol) of potassium carbonate, 0.8 g of potassium iodide, 36 ml of DMF and 7.72 g (27.7 mmol) of 4,4-bis(4-fluorophenyl)-3-butenyl chloride was stirred under nitrogen at 80°–90° for ½ hour and allowed to cool to room temperature. To the mixture was added 50 g (10.8 mmol) additional 4,4-bis(4-fluorophenyl)-3-butenyl chloride. The mixture was stirred at 40°–70° for 1 hour and subsequently at 80°–90° for 1 hour. The mixture was poured into ice/water/ether, extracted twice with ether, washed with water and saturated sodium chloride and dried over potassium carbonate. Filtration followed by evaporation of the solvent provided 13.9 g of an oil. The oil was dissolved in a minimum volume of ether and filtered through 200 g of alumina (eluent:ether). Evaporation of the solvent from the effluent provided 11.5 g of an oil. Recrystallization of the oxalate salt from methanol provided 2.31 g (4.15 mmol, 18.0%) of 1'-[4,4-bis(4-fluorophenyl)-3-butenyl]-5-chlorospiro[benzofuran-2(3H)4'-piperidine]oxalate, m.p. 210°–212° C.

ANALYSIS: Calculated for $C_{28}H_{26}ClF_2NO \cdot C_2H_2O_4$: 64.80%C, 5.08%H, 2.52%N; Found: 64.59%C, 5.18%H, 2.45%N.

EXAMPLE 5

1'-[4,4-Bis(4-fluorophenyl)butyl]-5-chlorospiro[benzofuran-2(3H)4'-piperidine]oxalate A suspension of 4.0 g (15.4 mmol) of 5-chlorospiro[benzofuran-2(3H)4'-piperidine]hydrochloride, 6.38 g (46.2 mmol) of potassium carbonate, 0.46 g of potassium iodide, 21 ml of DMF and 50.7 g, (18.1 mmol) of 4,4-bis(4-fluorophenyl)butyl chloride was stirred at room temperature for 40 hours under nitrogen. The mixture was poured into ice/saturated sodium carbonate, extracted twice with ether and washed with water and saturated sodium chloride. The ether solution was dried over potassium carbonate and filtered, and the solvent was evaporated to provide an oil. The oil was dissolved in ether and filtered through 175 g alumina (eluent:ether). Filtration followed by evaporation of the solvent provided an oil, the oxalate of which was crystallized from ethanol/methanol to provide in two crops 2.19 g (3.92 mmol, 25.5%) of 1'-[4,4-bis(4-fluorophenyl)butyl]-5-chlorospiro[benzofuran-2(3H)4'-piperidine]oxalate, m.p. 196°–198° C.

ANALYSIS: Calculated for $C_{28}H_{28}ClF_2NO \cdot C_2H_2O_4$: 64.57%C, 5.42%H, 2.51%N; Found: 64.44%C, 5.41%H, 2.41%N.

EXAMPLE 6

5-Iodospiro[benzofuran-2(3H)4'-piperidine]hydrochloride

A suspension of 10 g (44.3 mmol) of spiro[benzofuran-2(3H)4'-piperidine]hydrochloride, 200 ml of water, 200 ml of dichloromethane and 12.9 g (95%, 79.4 mmol) of iodine monochloride was vigorously stirred at an ambient temperature for 3.5 hours after which a solid precipitated from the reaction mixture. The solid was washed with water and dichloromethane and recrystallized from isopropyl alcohol to provide in two crops 6.31 g (17.9 mmol, 40.5%) of 5-iodospiro[benzofuran-2(3H)4'-piperidine]hydrochloride, m.p. 188°–191° C.

ANALYSIS: Calculated for $C_{12}H_{14}INO \cdot HCl$: 40.99%C, 4.30%H, 3.98%N; Found: 40.80%C, 4.25%H, 3.89%N.

EXAMPLE 7

1'-(4,4-Diphenylbutyl)-5-chlorospiro[benzofuran-2(3H)4'-piperidine]oxalate

A suspension of 6.81 (26.2 mmol) of 5-chlorospiro[benzofuran-2(3H)4'-piperidine]hydrochloride, 0.75 g of potassium iodide, 8.47 g (34.6 mmol) of 4,4-diphenylbutyl chloride, 33 ml of DMF and 11.2 g (81.7 mmol) of potassium carbonate was stirred at 80°–90° for 2.5 hours under nitrogen. The mixture was allowed to cool to room temperature, poured into ice/saturated sodium carbonate, extracted twice with ether, washed with water and saturated sodium chloride and dried over potassium carbonate. Filtration followed by evaporation of the solvent provided an oil. The oil was dissolved in a minimum volume of ether and filtered through 175 g of alumina (eluent:ether). Evaporation of the solvent from the effluent provided an oil. Crystallization of the oxalate from methanol provided 4.43 g (8.49 mmol, 32%) of 1'-(4,4-diphenylbutyl)-5-chlorospiro[benzofuran-2(3H)4'-piperidine]oxalate, m.p. 201°–212° C.

ANALYSIS: Calculated for $C_{28}H_{30}ClNO \cdot C_2H_2O_4$: 69.02%C, 6.18%H, 2.68%N; Found: 68.81%C, 6.10%H, 2.58%N.

EXAMPLE 8

1'-[4,4-Bis(4-fluorophenyl)butyl]-5-iodospiro[benzofuran-2(3H)4'-piperidine]hydrochloride A suspension of 2.7 g (7.68 mmol) of 5-iodospiro[benzofuran-2(3H)4'-piperidine]hydrochloride, 10 ml of DMF and 3.3 g (23.9 mmol) of potassium carbonate was stirred at 80°–90° under nitrogen for 2 hours. The mixture was allowed to cool to room temperature, poured into ice/ether, extracted twice with ether, washed with water and dried over potassium carbonate. Filtration followed by evaporation of the solvent provided an oil. The oil was dissolved in a minimum volume of ether and filtered through 175 g of alumina (eluent:ether). Evaporation of the solvent from the effluent provided an oil, the hydrochloride of which was crystallized from isopropyl alcohol to provide 4.15 g (6.96 mmol, 27%) of 1'-[4,4-bis(4-fluorophenyl)butyl]-5-iodospiro[benzofuran-2(3H)4'-piperidine]hydrochloride, m.p. 209°–211° C.

ANALYSIS: Calculated for $C_{28}H_{28}F_2INO \cdot HCl$: 56.43%C, 4.91%H, 2.35%N; Found: 56.24%C, 4.90%H, 2.20%N.

EXAMPLE 9

1'-(4,4-Diphenylbutyl)spiro[benzofuran-2(3H)4'-piperidine]hydrochloride

A suspension of 7.5 g (33.2 mmole) of spiro[benzofuran-2(3H)4'-piperidine]hydrochloride, 12.1 g (37.7 mmole) of potassium carbonate, 0.85 g of potassium iodide, 45 ml of DMF and 9.30 g (38.0 mmole) of 4,4-diphenylbutyl chloride was stirred at room temperature for 1 hour and at 80°–90° for 2.5 hours. The mixture was poured into ice/water, extracted twice with ether, washed with water and saturated sodium chloride and dried over potassium carbonate. Filtration followed by evaporation of the solvent provided 13.5 g of an oil. The oil was dissolved in ether and filtered through 200 g of alumina (eluent:ether). Evaporation of the solvent provided an oil, the hydrochloride of which was recrystallized from isopropyl alcohol to provide, in two crops, 3.12 g (7.19 mmole, 21.7%) of 1'-(4,4-diphenylbutyl)-spiro[benzofuran-2(3H)4'-piperidine]hydrochloride, m.p. 211°-213° C.

ANALYSIS: Calculated for $C_{28}H_{31}NO \cdot HCl$: 77.48%C, 7.43%H, 3.23%N; Found: 77.91%C, 7.42%H, 3.09%N.

We claim:

1. A compound of the formula

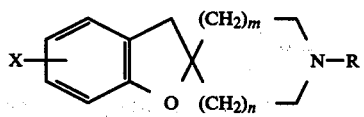

wherein X is hydrogen or halogen (F, Cl, Br, or I); m and n are each 0, 1 or 2 but m plus n is 1 or 2; and R is

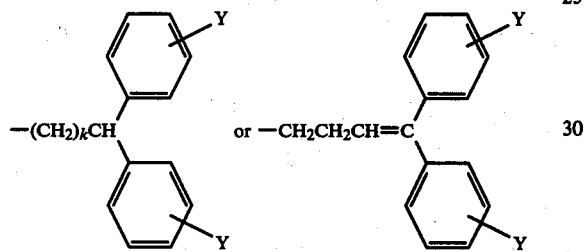

k being 2 or 3 and Y being hydrogen or halogen, or a pharmaceutically acceptable acid addition salt thereof.

2. The compound as defined in claim 1 where m is 1 and n is 1.

3. The compound as defined in claim 2 where m is 0 and n is 1.

4. The compound as defined in claim 1 where m is 2 and n is 0.

5. The compound as defined in claim 2 where X is hydrogen.

6. The compound as defined in claim 5 where R is

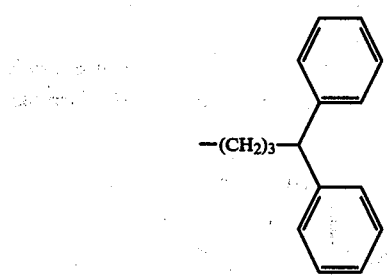

which is 1'-(4,4-diphenylbutyl)spiro[benzofuran-2(3H)4'-piperidine].

7. The compound as defined in claim 5 where R is

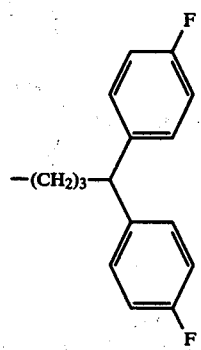

which is 1'-[4,4-bis(4-fluorophenyl)butyl]spiro[benzofuran-2(3H)4'-piperidine.

8. The compound as defined in claim 2 where X is chlorine.

9. The compound as defined in claim 8 where R is

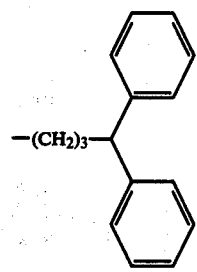

which is 1'-(4,4-diphenylbutyl)-5-chlorospiro[benzofuran-2(3H)4'-piperidine].

10. The compound as defined in claim 8 where R is

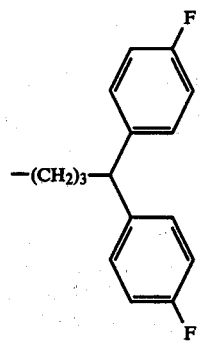

which is 1'-[4,4-bis(4-fluorophenyl) butyl]-5-chlorospiro[benzofuran-2(3H)4'-piperidine].

11. The compound as defined in claim 8 where R is

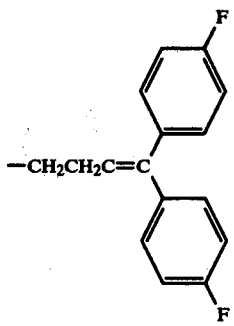

which is 1'-[4,4-bis(4-fluorophenyl)-3-butenyl]-5-chlorospiro[benzofuran-2(3H)4'-piperidine].

12. The compound as defined in claim 2 where X is bromine.

13. The compound as defined in claim 12 where R is

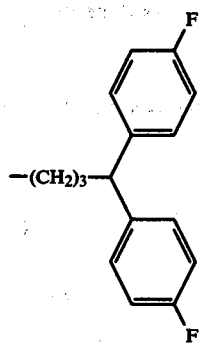

which is 1'-[4,4-bis(4-fluorophenyl)butyl]-5-bromospiro[benzofuran-2(3H)4'-piperidine].

14. The compound as defined in claim 2 where X is iodine.

15. The compound as defined in claim 14 where R is

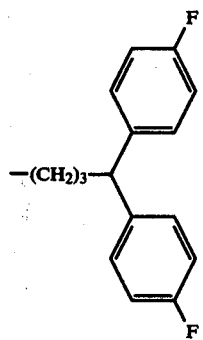

which is 1'-[4,4-bis(4-fluorophenyl)butyl]-5-iodospiro[benzofuran-2(3H)4'-piperidine].

16. An antihypertensive composition comprising an effective amount of a compound of the formula

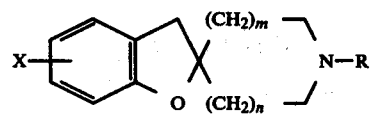

wherein X is hydrogen or halogen (F, Cl, Br, or I); m and n are each 0, 1 or 2 but m plus n is 1 or 2; and R is

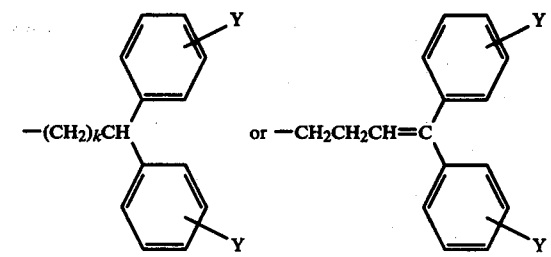

k being 2 or 3 and Y being hydrogen or halogen, or a pharmaceutically acceptable acid addition salt thereof.

17. The antihypertensive composition as defined in claim 16 where m is 1 and n is 1.

18. The antihypertensive composition as defined in claim 16 where m is 1 and n is 0.

19. A method of preparing a compound of the formula

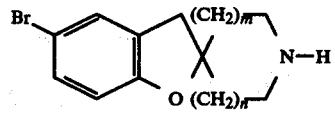

where m and n are each 0, 1 or 2 but m plus n is 1 or 2, which comprises reacting a compound of the formula

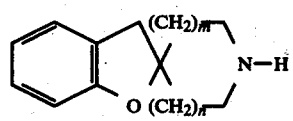

with N-bromosuccinimide to afford said compound.

20. A method of preparing a compound of the formula

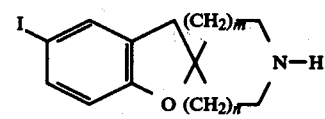

where m and n are each 0, 1 or 2 but m plus n is 1 or 2, which comprises reacting a compound of the formula

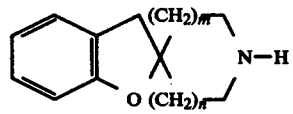

with iodine monochloride to afford said compound.

21. A method of preparing a compound of the formula

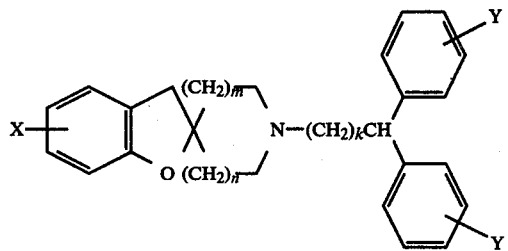

where X is hydrogen or halogen (F, Cl, Br, or I); m and n are each 0, 1 or 2 but m plus n is 1 or 2; k is 2 or 3; and Y is hydrogen or halogen, which comprises reacting a compound of the formula

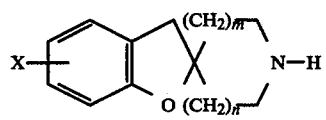

with a compound of the formula

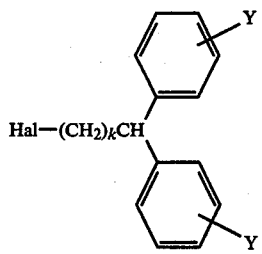

Hal being chlorine or bromine, to afford said compound.

22. The method as defined in claim 21, where m is 1.
23. The method as defined in claim 22, where n is 1.

24. A method of preparing a compound of the formula

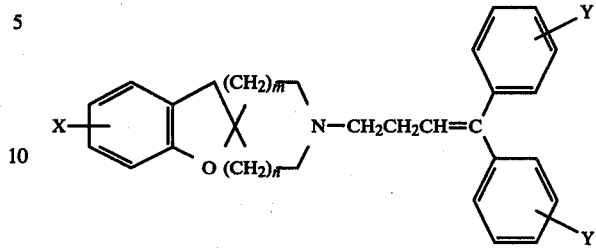

where X is hydrogen or halogen (F, Cl, Br, or I); m and n are each 0, 1 or 2 but m plus n is 1 or 2; and Y is hydrogen or halogen, which comprises reacting a compound of the formula

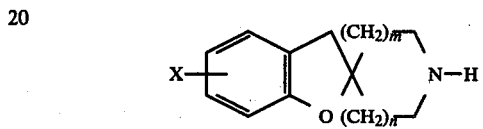

with a compound of the formula

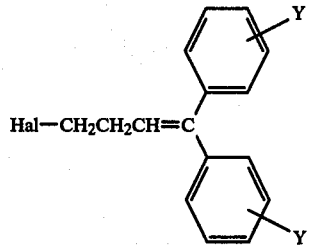

Hal being chlorine or bromine, to afford said compound.

25. The method as defined in claim 24, where m is 1.
26. The method as defined in claim 25, where n is 1.

* * * * *

UNITED STATES PATENT AND TRADEMARK OFFICE
CERTIFICATE OF CORRECTION

PATENT NO. : 4,452,802

DATED : June 5, 1984

INVENTOR(S) : Raymond W. Kosley, Jr. & Robert J. Cherill

It is certified that error appears in the above—identified patent and that said Letters Patent is hereby corrected as shown below:

Claim 3, line 1, "defined in Claim 2" should read --defined in Claim 1--.

Signed and Sealed this

Sixth Day of November 1984

[SEAL]

Attest:

GERALD J. MOSSINGHOFF

Attesting Officer

Commissioner of Patents and Trademarks